(12) United States Patent
Ueberschlag et al.

(10) Patent No.: US 10,199,028 B2
(45) Date of Patent: Feb. 5, 2019

(54) ULTRASONIC TRANSDUCER MOUNTING ASSEMBLY

(71) Applicant: Endress + Hauser Flowtec AG, Reinach (CH)

(72) Inventors: Pierre Ueberschlag, Saint-Louis (FR); Michal Bezdek, Aesch (CH); Andreas Berger, Hasel-Glashutten (DE)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 3 days.

(21) Appl. No.: 14/893,105

(22) PCT Filed: Apr. 25, 2014

(86) PCT No.: PCT/EP2014/058441
§ 371 (c)(1),
(2) Date: Nov. 23, 2015

(87) PCT Pub. No.: WO2014/187645
PCT Pub. Date: Nov. 27, 2014

(65) Prior Publication Data
US 2016/0093280 A1    Mar. 31, 2016

(30) Foreign Application Priority Data

May 21, 2013   (DE) .................. 10 2013 105 169
May 24, 2013   (DE) .................. 10 2013 105 329

(51) Int. Cl.
*G01F 15/18*    (2006.01)
*G01N 29/22*    (2006.01)
(Continued)

(52) U.S. Cl.
CPC ............ *G10K 11/004* (2013.01); *G01F 1/662* (2013.01); *G01F 15/18* (2013.01); *G01N 29/222* (2013.01); *G01N 29/223* (2013.01)

(58) Field of Classification Search
CPC ....... G10K 11/004; G01F 1/662; G01F 15/18; G01N 29/222; G01N 29/223
(Continued)

(56) References Cited

U.S. PATENT DOCUMENTS 3,511,323 A *   5/1970   Riley, Jr. .............. G10K 11/004
                                              126/41 R
5,038,612 A     8/1991   Thelen
(Continued)

FOREIGN PATENT DOCUMENTS

DE   3941634 A1   6/1991
DE   4443415 A1   6/1996
(Continued)

OTHER PUBLICATIONS

International Search Report, EPO, The Netherlands, dated Jul. 7, 2014.
(Continued)

*Primary Examiner* — Manish S Shah
*Assistant Examiner* — Rose M Miller
(74) *Attorney, Agent, or Firm* — Bacon & Thomas, PLLC

(57) ABSTRACT

Disclosed is an ultrasonic transducer mounting assembly comprising an ultrasonic transducer element, a transducer housing inside which the ultrasonic transducer element is arranged, and an accommodation unit inside which the transducer housing is clamped in a clamping section. The disclosed assembly is characterized in that the clamping section comprises at least one bearing that has at least one rolling element, in particular at least one ball bearing that has at least one ball, for acoustically decoupling the transducer housing from the accommodation unit.

11 Claims, 7 Drawing Sheets

(51) Int. Cl.
*G10K 11/00* (2006.01)
*G01F 1/66* (2006.01)

(58) Field of Classification Search
USPC .................................................. 73/617, 644
See application file for complete search history.

(56) References Cited

U.S. PATENT DOCUMENTS

| | | | |
|---|---|---|---|
| 5,477,729 A * | 12/1995 | Cavalloni | G01H 11/08 73/514.34 |
| 5,602,718 A | 2/1997 | Peszynski | |
| 5,626,138 A | 5/1997 | Hossack | |
| 5,737,963 A | 4/1998 | Eckert et al. | |
| 5,814,736 A | 9/1998 | Loschberger | |
| 7,080,543 B2 | 7/2006 | Ishikawa | |
| 8,127,613 B2 | 3/2012 | van Klooster | |
| 8,939,034 B2 | 1/2015 | Berger | |
| 2011/0314933 A1 * | 12/2011 | Mueller | B06B 1/0655 73/861.18 |

FOREIGN PATENT DOCUMENTS

| | | |
|---|---|---|
| DE | 19723488 A1 | 12/1998 |
| DE | 102007022513 A1 | 11/2008 |
| DE | 102009039633 A1 | 3/2011 |
| DE | 102010064119 A1 | 6/2012 |
| EP | 0384949 A2 | 9/1990 |
| EP | 2146190 A1 | 1/2010 |
| WO | 9618181 A1 | 6/1996 |

OTHER PUBLICATIONS

English Translation of the International Preliminary Report on Patentability, WIPO, Geneva, CH, dated Dec. 3, 2015.

* cited by examiner

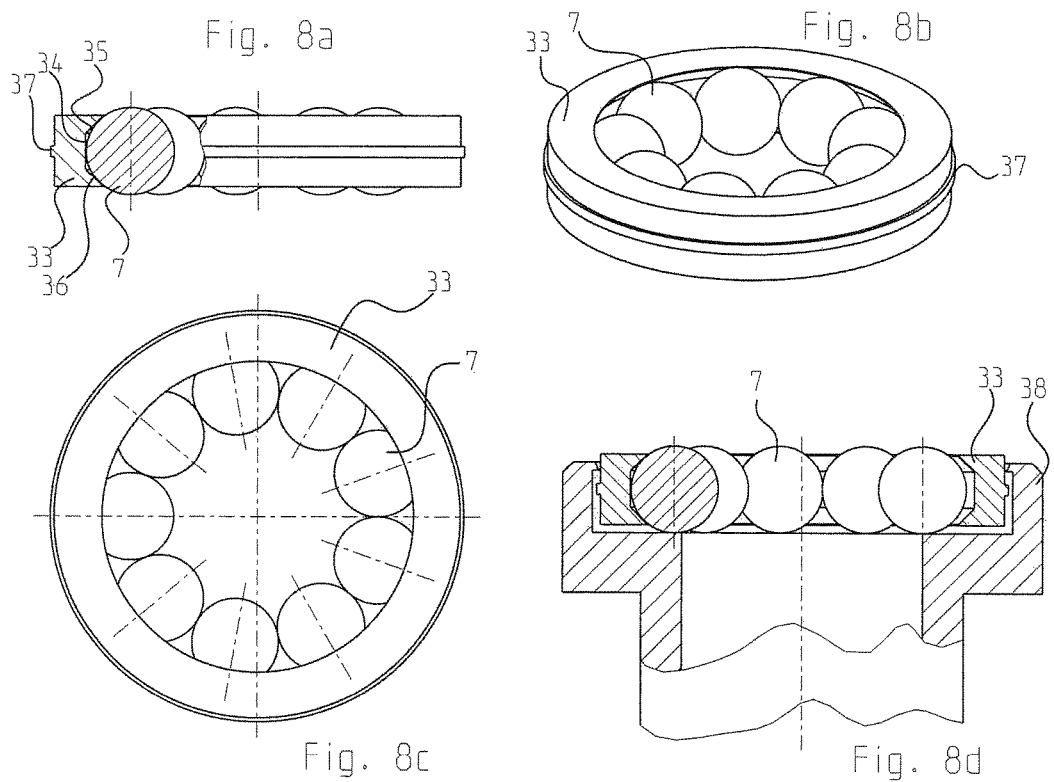
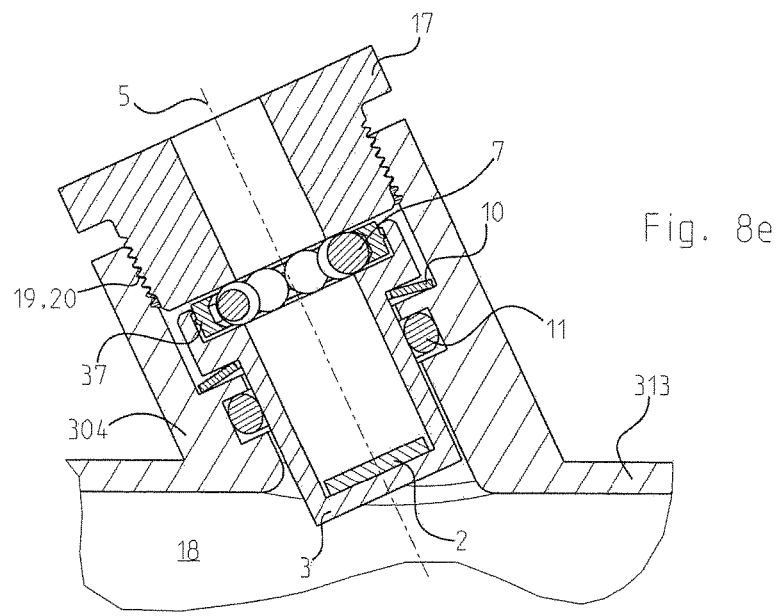

ULTRASONIC TRANSDUCER MOUNTING ASSEMBLY

TECHNICAL FIELD

The invention relates to an ultrasonic transducer mounting assembly.

BACKGROUND DISCUSSION

Ultrasonic flow meters are often used in process and automation technology. They allow determination of the volumetric flow rate and/or mass flow in a pipeline in a simple way. Known ultrasonic flow meters often work according to the runtime difference principle. In the runtime difference principle, the different runtimes of ultrasonic waves, in particular ultrasonic pulses, so-called bursts, are evaluated relative to the direction of flow of the liquid. To this end, ultrasonic pulses are transmitted at a certain angle to the pipe axis, both in and against the direction of flow. Using the runtime difference, the flow rate and thus the volumetric flow rate can be determined if the diameter of the pipeline section is known.

The ultrasonic waves are generated or received by means of so-called ultrasonic transducers. For this purpose, ultrasonic transducers are firmly attached to the pipe wall of the relevant pipeline section. Clamp-on ultrasonic flow measurement systems are also available. In these systems, the ultrasonic transducers are pressed from outside of the measuring tube against the tube wall. A big advantage of clamp-on ultrasonic flow measurement systems is that they do not touch the measurement medium and can be mounted on an existing pipeline.

The ultrasonic transducers usually consist of an electromechanical transducer element, e.g. a piezoelectric element, and a coupling layer. In clamp-on systems, the ultrasonic waves are generated as acoustic signals in the electromechanical transducer element, and passed over the coupling layer to the pipe wall and then into the liquid. In inline systems, the acoustic signals are coupled to the measurement medium via the coupling layer.

Both in clamp-on systems as well as inline systems, the ultrasonic transducers are usually arranged in a common plane on the measuring tube, either on opposite sides of the measuring tube, in which case the acoustic signal traverses the measuring tube once along a secant, projected onto a tube cross-section, or on the same side of the measuring tube, in which case the acoustic signal is reflected at the opposite side of the measuring tube, whereby the acoustic signal traverses the measuring tube twice along the secant projected onto the cross-section through the measuring tube.

Two processes take place in the runtime difference principle. In the first process, a first ultrasonic transducer transmits acoustic signals that propagate through the medium to the measuring tube. The acoustic signals are received by a second ultrasonic transducer. In the second process, the second ultrasonic transducer transmits acoustic signals that are received by the second ultrasonic transducer. If a medium flows through the measuring tube, the first and the second processes result in different runtimes. The flow rate of the medium in the measuring tube is determined from these two runtimes.

Besides the acoustic signal, the transmitting ultrasonic transducer also generates an acoustic noise that is transmitted from an ultrasonic transducer housing to the measuring tube and to the receiving ultrasonic transducer via the measuring tube. Conventionally, the ultrasonic transducer housing with dampers made of polymers or elastomers is decoupled from the measuring tube to minimize the transmission of the acoustic noise. However, polymers or elastomers are of low strength and durability.

SUMMARY OF THE INVENTION

The object of the invention is to provide an ultrasonic transducer mounting assembly, wherein the acoustic coupling between the transducer housing and the measuring tube is reduced, wherein the ultrasonic transducer mounting assembly has a high strength and a high durability at the same time.

The object is achieved by an ultrasonic transducer mounting assembly which includes an ultrasonic transducer element, a transducer housing, in which the ultrasonic transducer element is arranged, and an accommodation unit, wherein the transducer housing is clamped in a clamping path in the accommodation unit, wherein the clamping path according to the invention comprises at least one bearing with at least one rolling element, in particular at least one ball bearing with at least one ball for acoustic decoupling of the transducer housing from the accommodation unit.

The clamping path is generally defined as an arrangement of elements that are mutually clamped. By using rolling elements, the contact surface between the transducer housing and accommodation unit is minimized, whereby the acoustic coupling of the transducer housing and the accommodation unit is minimized. If the rolling elements comprise balls, the sound reaches the ball over a quasi point-shaped contact between the accommodation unit and the ball, and spreads out in all directions. The acoustic waves are predominantly reflected on a side of the ball opposite the entry point, as only a quasi point-shaped contact exists between the ball and the accommodation unit at this side of the ball as well. The sound waves that have entered the ball are reflected in the ball until the sound waves have waned. The bearing may be designed movable or rigid due to the rolling elements.

According to one embodiment, the transducer housing comprises at least a first clamping surface and the accommodation unit comprises at least a second clamping surface, wherein a bearing is formed from a clamping surface of the transducer housing and a clamping surface of the accommodation unit, as well as rolling elements between the two clamping surfaces.

According to one embodiment, the rolling elements of the bearing are barrel-shaped.

According to one embodiment, the transducer housing is pre-tensioned in the clamping path in the accommodation unit by at least one spring, in particular, by at least one disk spring and/or at least one helical spring.

According to one embodiment, the rolling elements of the bearing are made of metal, ceramic, plastic, glass or a composite.

According to one embodiment, the transducer housing comprises a first and a second clamping surface and the accommodation unit comprises a first and a second clamping surface, wherein a first bearing is formed of rolling elements between the first clamping surface of the transducer housing and the first clamping surface of the accommodation unit and a second bearing is formed of rolling elements between the second clamping surface of the transducer housing and the second clamping surface of the accommodation unit.

For easy assembly and disassembly of the mounting assembly, it is advantageous if the bearing comprises a plurality of rolling elements which are held by a bearing ring, or in particular, a cylindrical cover. Alternative cover designs are also conceivable, e.g. oval covers. In this case, the bearing ring can be part of the bearing. The cover may rather be attributed to the transducer housing. Preferably, the inner wall of the cover itself forms the holder of the rolling elements. The arrangement in the cover has the added benefit of material savings.

It is advantageous if the bearing ring or the cover comprises a central axis, and the rolling elements are held such that a radial movement of the rolling elements is blocked or limited relative to the central axis. This allows use of the rolling elements in the mounting assembly as a so-called rolling element package.

Blockage or limitation may take place by the interaction between the rolling elements themselves, leading to material savings. Alternatively, a central holder, preferably a ring, may carry out the blockage or limitation. This is arranged within the bearing ring. Here, the bearing can be formed as a standard ball bearing, which is commercially available as a mass product in different sizes at an affordable price. In particular in case of the cover design, an O-ring that is arranged inside the bearing ring of the cover, e.g. in an annular groove, may be used.

The object of the invention is also achieved by an ultrasonic measurement arrangement, which comprises an ultrasonic transducer mounting assembly according to the invention, wherein the ultrasonic transducer mounting assembly is mounted on a measuring tube or a tank, wherein the ultrasonic transducer mounting assembly is connected with an evaluation unit for evaluation of the time-related characteristics of the acoustic signal.

According to one embodiment of the ultrasonic measurement arrangement, the accommodation unit protrudes at least partially into the measuring tube or the tank.

The object of the invention is also achieved by an ultrasonic flow meter with an ultrasonic measurement arrangement according to the invention. The ultrasonic flow meter according to the invention comprises at least a first and a second ultrasonic transducer mounting assembly according to the invention, which are arranged on the measuring tube in such a way that ultrasonic signals can be transmitted from a first ultrasonic transducer of the first ultrasonic transducer mounting assembly to a second ultrasonic transducer of the second ultrasonic transducer mounting assembly, and vice versa, via the volume of the measuring tube, through which the medium flows.

BRIEF DESCRIPTION OF THE DRAWINGS

The invention is further illustrated, based on the following drawings. Illustrated are:

FIG. 8a to FIG. 8e: shows a bearing for a fourth ultrasonic transducer mounting assembly according to the invention;

DETAILED DISCUSSION IN CONJUNCTION WITH THE DRAWINGS

Figure 1:
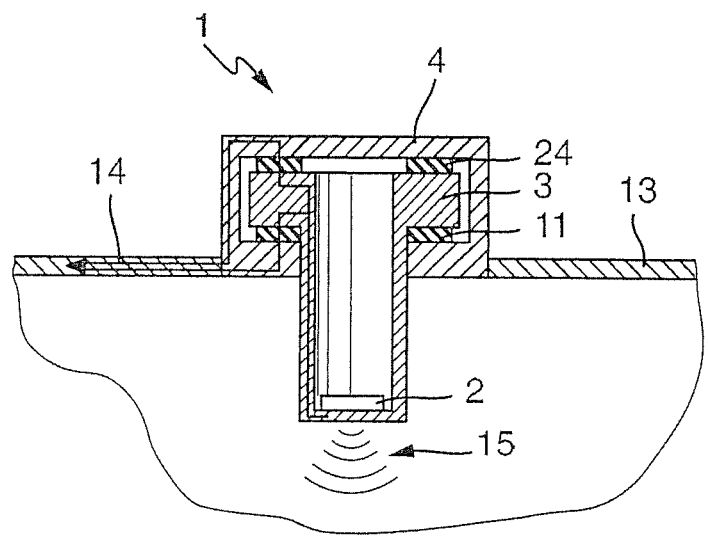
FIG. 1: is a longitudinal section of an ultrasonic transducer mounting assembly according to the prior art.

FIG. 1 shows a longitudinal section of an ultrasonic transducer mounting assembly 1 according to the prior art. A hollow cylindrical transducer housing 3 comprises an ultrasonic transducer element 2 at an inner first front face. The ultrasonic transducer element 2 is formed of a piezo-electric material to transmit acoustic signals 15 through the first front face of the transducer housing 3. The transducer housing 3 comprises a flange 27 at an end portion of the transducer housing 3 opposite the first front face of the transducer housing 3. The transducer housing 3 protrudes partially into a measuring tube 13, so that the ultrasonic transducer element 2 is arranged in the measuring tube 13 and the flange 27 is arranged outside of the measuring tube 13. The part of the transducer housing 3 protruding from the measuring tube 13 is surrounded by an accommodation unit 4, said accommodation unit 4 being cylindrical and arranged on a first front face of the measuring tube 13. Within the accommodation unit 4, the flange 27 is held in place by means of a first and a second O-ring 11, 24, wherein the first O-ring 11 is arranged between an inner surface of the accommodation unit 4 adjoining the measuring tube 13, and the flange 27, and the second O-ring 24 is arranged between the flange 27 and an inner front face of the accommodation unit 4 opposite the measuring tube 13.

The ultrasonic transducer 2 emits ultrasonic signals 15 that propagate in the medium of the measuring tube 13 and reach a second ultrasonic transducer of a second ultrasonic transducer mounting assembly for runtime determination. The ultrasonic signals 15 propagate also through the transducer housing 3, the accommodation unit 4 and the measuring tube 13 in the form of acoustic noise 14. This noise 14 is suppressed according to the invention.

Figure 2:
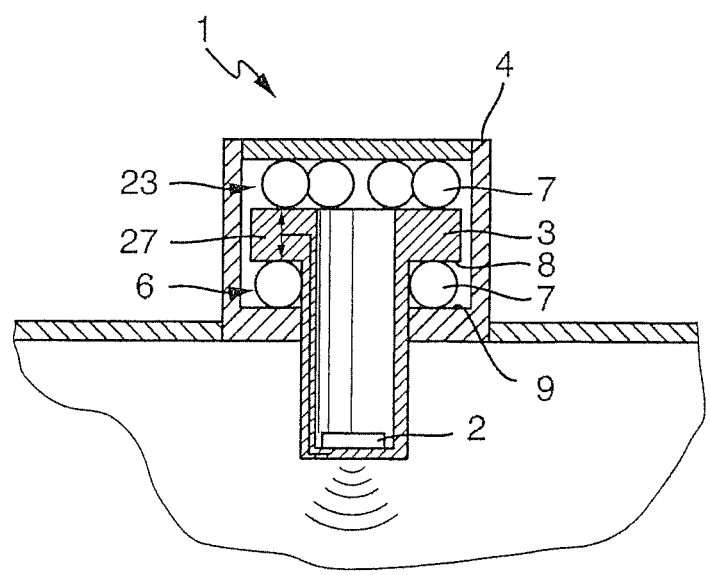
FIG. 2: is a longitudinal section of a first ultrasonic transducer mounting assembly according to the invention.

FIG. 2 shows a longitudinal section of an ultrasonic transducer mounting assembly according to the invention. Instead of the first and the second O-ring 11, 24 of the embodiment according to FIG. 1, the flange 27 is held in place by ball-shaped rolling elements 7 in the accommodation unit 4. The rolling elements 7, the accommodation unit 4 and the transducer housing 3 are metallic, in particular, made of steel.

The inner front face of the accommodation unit 4 adjoining the measuring tube 13 defines a first clamping surface 9 of the accommodation unit 4. The side of the flange 27 facing the measuring tube 13 defines a first clamping surface 8 of the transducer housing 3. The first clamping surface 8 of the transducer housing 3 and the first clamping surface 9 of the accommodation unit 4 with the interspersed rolling elements 7 define a first bearing 6, whose rolling elements are pivot-mounted between the flange 27 and the inner front face of the accommodation unit 4 adjoining the measuring tube 13. However, this rotatability is not relevant to the present invention.

The surface of the flange 27 facing away from the measuring tube 13 defines a second clamping surface 28 of the transducer housing 3. The inner surface of the accommodation unit 4 facing the measuring tube 13 defines a second clamping surface 29 of the accommodation unit 4. The second clamping surface 28 of the transducer housing 3 and the second clamping surface 29 of the first accommodation unit 4, together with the interspersed rolling elements 7, define a second bearing 23.

The rolling elements 7 of the first and the second bearings 6, 23 are mounted such that the transducer housing 3 is mounted, so as to be able to rotate about its longitudinal axis 5. Independently of the first and the second bearings 6, 23, a third bearing, which is not shown here, can be arranged radially on the flange 27.

In this way, the mounting of the transducer housing 3 in the accommodation unit 4 shows a high strength and a high durability, and at the same time, the quasi point-shaped contacts between the rolling elements 7 and the accommodation unit 4 or the flange 27 of the transducer housing 3, show constriction of the sound path, so that the noise 14 of the acoustic signal is largely suppressed.

Figure 3:
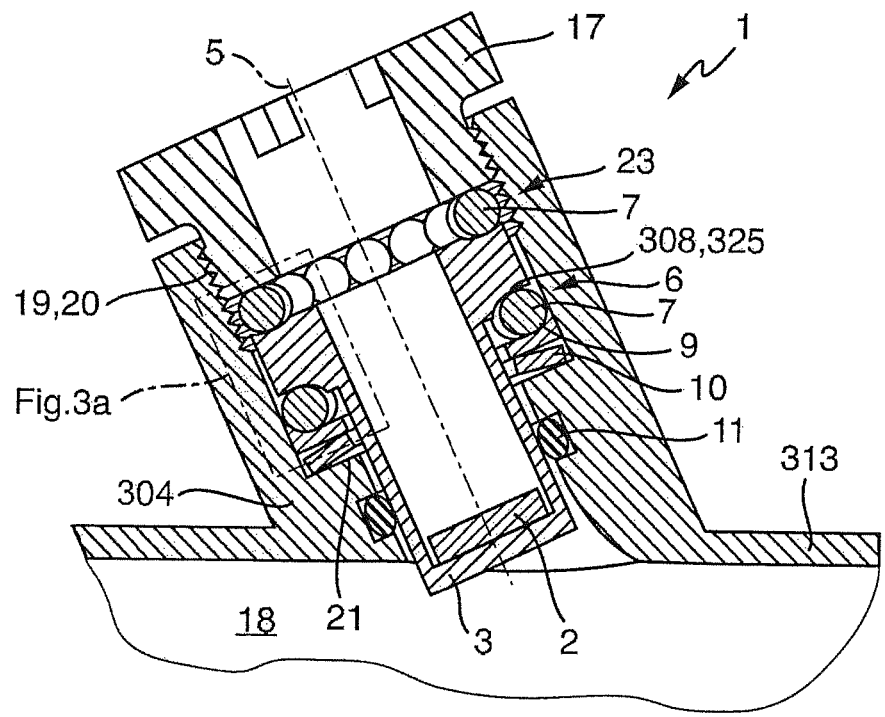
FIG. 3: is a longitudinal section of an ultrasonic transducer mounting assembly according to the invention, which is integrated in a measuring tube.
Figure 3A:
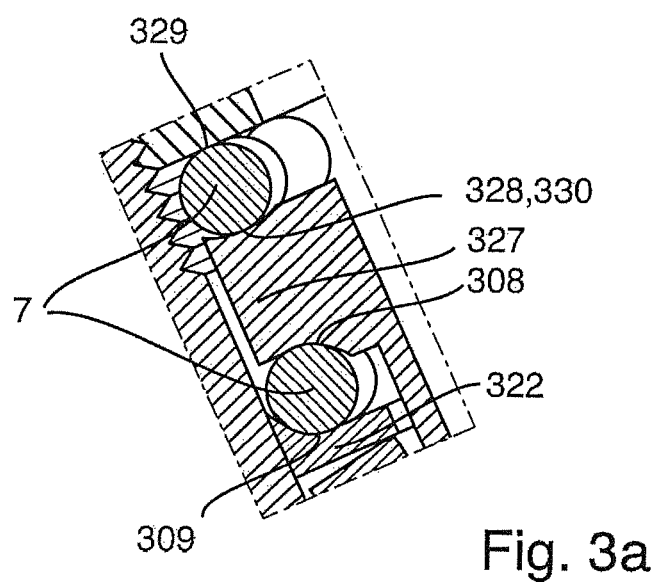
FIG. 3a: is a longitudinal section of an enlarged portion of the ultrasonic transducer mounting assembly integrated in a measuring tube.

FIG. 3 and FIG. 3a show a longitudinal section and an enlarged detail of a longitudinal section respectively of an embodiment of the ultrasonic mounting arrangement 1 according to the invention, which is integrated in a measuring tube 313 according to the general structure shown in FIG. 2. In this embodiment, an accommodation unit 304 and the measuring tube 313 are formed as a single unit. A longitudinal axis 5 of the transducer housing 3 is arranged at an angle to a longitudinal axis of the measuring tube 313. The accommodation unit 304 has a longitudinal axis 5, which coincides with the longitudinal axis 5 of the transducer housing 3.

Within the accommodation unit 304, an annular first shoulder 21, which holds the flange 327 is arranged, so as to properly fit the flange 327. A disk spring 10, a shoulder ring 322 and rolling elements 7 are arranged between the flange 327 and the first shoulder 21. In the direction of the measuring tube 313, the flange 327 comprises a second shoulder 325, which defines a first clamping surface 308 of the transducer housing 3. The shoulder ring 322 has an annular recess, which defines a first clamping surface 309 of the accommodation unit 304. The first clamping surface 308 of the transducer housing 3 and the first clamping surface 309 of the first accommodation unit 304, together with the interspersed rolling elements 7, define the first bearing 6.

An O-ring 11 is arranged in a portion between the first shoulder 21 and the measuring tube 313, so that a medium 18 from the measuring tube 313 cannot enter the interior of the accommodation unit 304. The O-ring 11 is, in particular, clamped between a lateral surface of the transducer housing and an opposite wall of the accommodation unit 304.

A first thread 19 is arranged at a second end portion of the accommodation unit 304 opposite the measuring tube 313. A hold-down device 17, which has a second thread 20 matching the first thread 19, closes the accommodation unit 304 at the second end portion. Rolling elements 7 are arranged between the hold-down device 17 and the flange 327.

A first annular groove 30, which defines a second clamping surface 328 of the transducer housing 3, is arranged at a front face of the transducer housing 3 facing away from the measuring tube 313. A front face of the hold-down device 17 facing the measuring tube 313 defines a second clamping surface 329 of the accommodation unit 4. The second clamping surface 328 of the transducer housing 3 and the second clamping surface 329 of the accommodation unit 4, together with the interspersed rolling elements 7, define the second bearing 23.

In order to produce a virtually point-shaped contact between the rolling elements 7 and their clamping surfaces 308, 309, 328, 329, the clamping surfaces 308, 309, 328, 329 have a larger radius of curvature than that of the rolling elements 7.

When screwing the accommodation unit 304 to the hold-down device 17, pressure is applied on the rolling elements 7 of the second bearing 23, wherein this pressure is transmitted to the transducer housing 3 and the rolling elements 7 of the first bearing 6, and thus to the shoulder ring 322 and the disk spring 10. Here, the disk spring 10 yields under pressure and the transducer housing 3 is clamped in the direction of its longitudinal axis 5 between the rolling elements 7 of the first and the second bearings 6, 23.

Figure 4:
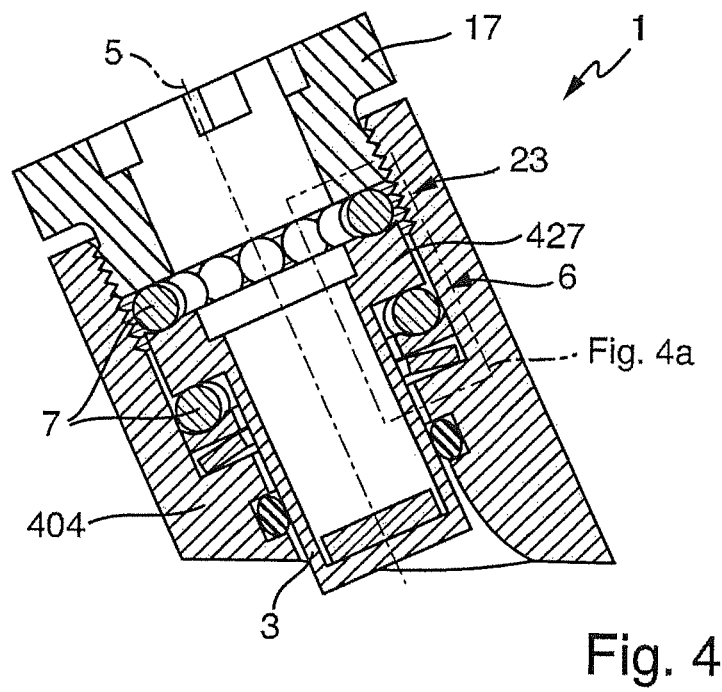
FIG. 4: is a longitudinal section of another embodiment of an ultrasonic transducer mounting assembly according to the invention.
Figure 4A:
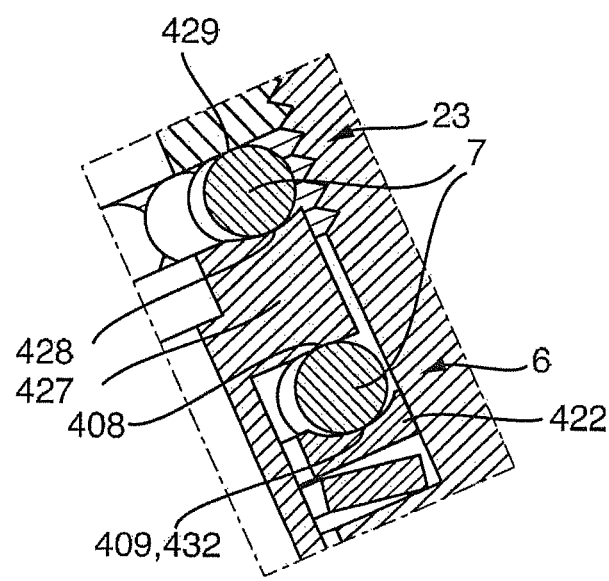
FIG. 4a: is a longitudinal section of an enlarged portion of a ball bearing of an ultrasonic transducer mounting assembly according to FIG. 4.

FIG. 4 and FIG. 4a show a longitudinal section and an enlarged detail of a longitudinal section respectively of another embodiment of an ultrasonic transducer mounting assembly 1 according to the invention corresponding to FIG. 3. In this embodiment, a first clamping surface 408 of the transducer housing 3, which is facing a measuring tube 313, is planar in form. Rolling elements 7 of a first bearing 6 are clamped against the clamping surface 408. A shoulder ring 422 is arranged on a side of the rolling elements 7 of the first bearing 6 opposite the clamping surface 408. The shoulder ring 422 has an annular second groove 432, which defines the first clamping surface 409 of the accommodation unit 404. The rolling elements 7 of the first bearing 6 have a more or less point-shaped contact with the first clamping surface 409 of the accommodation unit 404.

Figure 5:
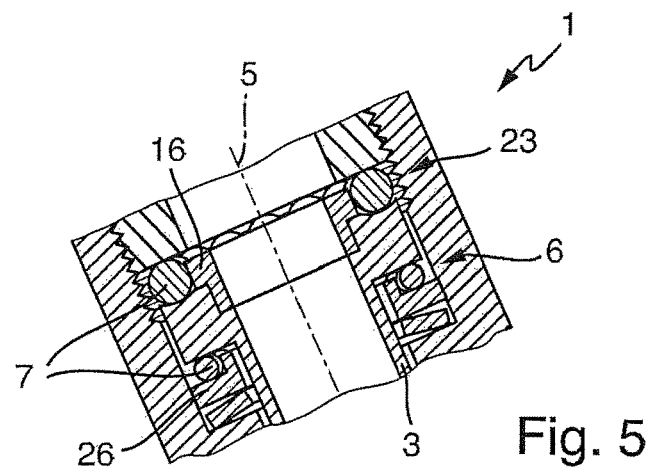
FIG. 5: is a longitudinal section of another embodiment of an ultrasonic transducer mounting assembly according to the invention with a centering ring.

FIG. 5 shows a longitudinal section of another embodiment of an ultrasonic transducer mounting assembly 1 according to the invention with a first and a second centering ring 16, 26. The first centering ring 16 is arranged on a front face of a transducer housing 3 facing away from the measuring tube 13, and ensures that the rolling elements 7 of a second bearing 23 are held in a predefined path around the longitudinal axis 5 of the transducer housing 3. The second centering ring 26 replaces the shoulder ring 22 shown in FIGS. 3 and 4, and ensures that the rolling elements 7 of the first bearing 6 are held in a predefined path around the longitudinal axis 5 of the transducer housing 3.

Figure 6:
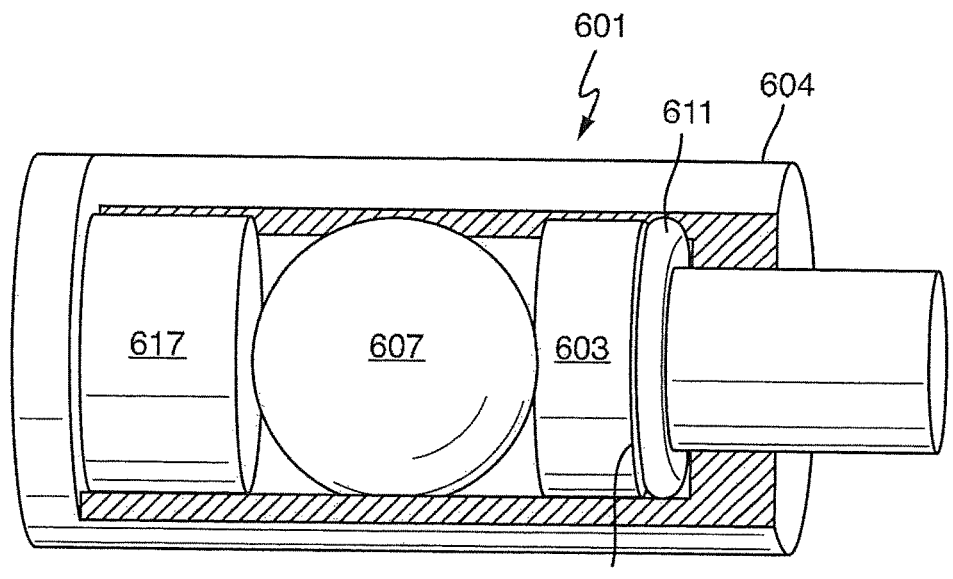
FIG. 6: is a second ultrasonic transducer mounting assembly according to the invention with only one rolling element.

FIG. 6 shows an ultrasonic transducer mounting assembly 1 with only one spherical rolling element 607. At an end portion facing a measuring tube 13, an accommodation unit 604 includes a constriction, in which a cylindrical portion of the transducer housing 603 is arranged. The transducer housing 603 comprises a flange 627 at an end portion that is arranged in the accommodation unit 604. An O-ring 11 is axially clamped between the flange 627 and a radial part of the constriction of the accommodation unit 604, so that a medium 18 from the measuring tube 13 cannot enter the interior of the accommodation unit 604. A spherical rolling element 607 is arranged at a front face of the transducer housing 603 opposite the measuring tube 13. At an end portion of the accommodation unit opposite the transducer housing 603, a hold-down device 617 closes the accommodation unit 604 and tensions the rolling elements 607 against the flange 627.

Figure 7:
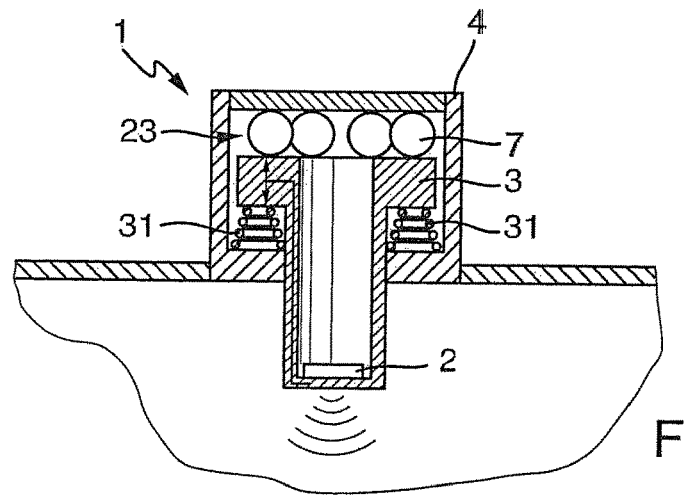
FIG. 7: is a third ultrasonic transducer mounting assembly according to the invention.

FIG. 7 shows an ultrasonic transducer mounting assembly 1 according to FIG. 2, wherein a plurality of helical springs 31 are arranged between the flange 27 of the transducer housing 3 and an inner surface of the accommodation unit 4 adjoining the measuring tube 13. The helical springs 31 act resiliently along the clamping path, so that the flange 27 remains clamped along the clamping path in different thermal expansions of the accommodation unit 4, flange 27 or rolling elements 7.

The ultrasonic transducer mounting assembly according to the invention can be used both for measuring a flow rate in a measuring tube as well as for measuring a fill level in a tank. For this purpose, it is advantageous to arrange the ultrasonic transducer mounting assembly in an ultrasonic measurement arrangement and establish an electrical connection with an evaluation unit for evaluation of the time-related characteristics of the acoustic signal.

The bearings 6 and 23 shown in FIGS. 2-5 and 7 can be arranged individually or, particularly advantageously, comprise a bearing ring 33 to simplify assembly and disassembly of the mounting assembly. Two preferred embodiments of several embodiments are shown in FIGS. 8*a-e*) and 9*a*)-*d*).

bearing cages and bearing rings for rolling elements are known in many ways. They are used to reduce friction between rotating bodies and fixed bearing blocks. In order to protect the gaps between the rolling elements 7, e.g. from abrasion or contamination, bearings mostly have an inner and an outer bearing ring.

An inner ring may be omitted in the bearing 6 and 23, so as to lead to material savings, as the contamination of gaps between the rolling elements and rotational movements are not of primary importance in this case.

The bearing ring 33 has a U-shaped inner contour 34. Two legs 35 and 36 are respectively perpendicular or parallel to the surface of each rolling element 7. The circumference of the bearing ring 33 is dimensioned such that the rolling elements 7 are intermeshed and are present in a press fit.

The bearing ring 33 may be made of metal. Attention must be paid to a proper fit in this case. However, the bearing ring 33 may preferably consist of a plastic material. In this way, the sound is also attenuated toward the side of the rolling elements 7. In order to allow greater manufacturing tolerances, the bearing ring may be made of an elastomer, so that the circumference of the bearing ring can be widened for a better arrangement of the rolling elements 7.

The outer circumference of the bearing ring 33 has a circumferential stop ring 37, which limits the range of motion of the entire bearing in relation to the axial axis of the ultrasonic mounting assembly. The movement of the bearing radially to the axial axis of the ultrasonic mounting assembly is limited by a holder 38, which is preferably part of the accommodation unit 4 or the transducer housing 3.

In FIG. 8*e*), the bearing of FIGS. 8*a*)-8*d*) is shown as part of an ultrasonic transducer mounting assembly.

Figure 9A:
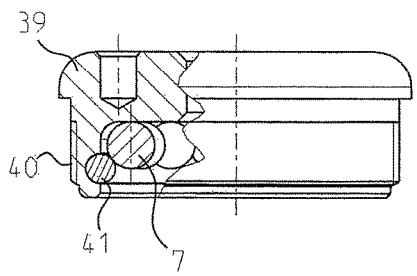
FIG. 9a to FIG. 9d: shows a bearing for a fifth ultrasonic transducer mounting assembly according to the invention.
Figure 9B:
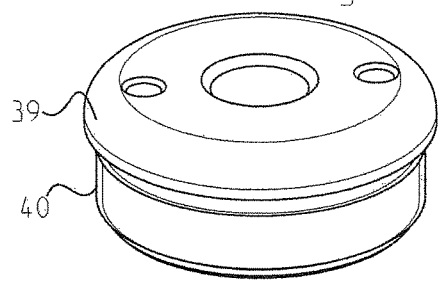
Figure 9C:
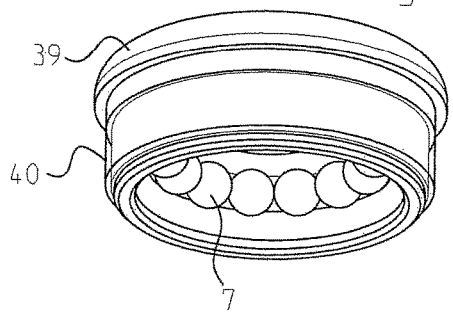

In FIG. 9*a*)-9*d*), an exemplary embodiment is shown, in which the bearing ring forms the cover 39 of the transducer housing 3 and/or the hold-down device at the same time. The rolling elements 7 are arranged along the inner circumference of the bearing ring 39 and/or the cover and block each other in the radial direction due to their dead volume. In the axial direction, the movement of the rolling elements is prevented by a stop 41. This is preferably arranged circumferentially at the inner circumference of the cover 39 and may be formed, for example as an O-ring of an elastomer, e.g. rubber. It is also possible to create a corresponding stop in the cover, for example by a deep-drawing process, or weld it on the inner circumference of the lid. Particularly preferably, the cover has an inner circumferential, annular groove 42, in which the O-ring is inserted and thus positioned.

Figure 9D:
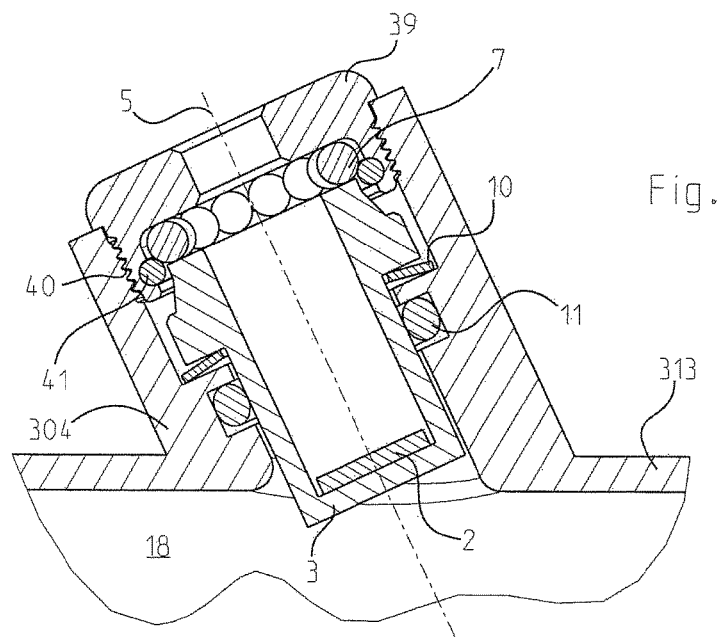

The cover also has an external thread 40 to form a unit with the rest of the transducer housing by screwing to it. In FIG. 9*d*), an ultrasonic transducer mounting assembly is shown with the bearing shown in FIG. 9*a*)-*c*).

The embodiments shown in the FIGS. 8 and 9 are just examples, and other geometric modifications are possible.

Figure 10:
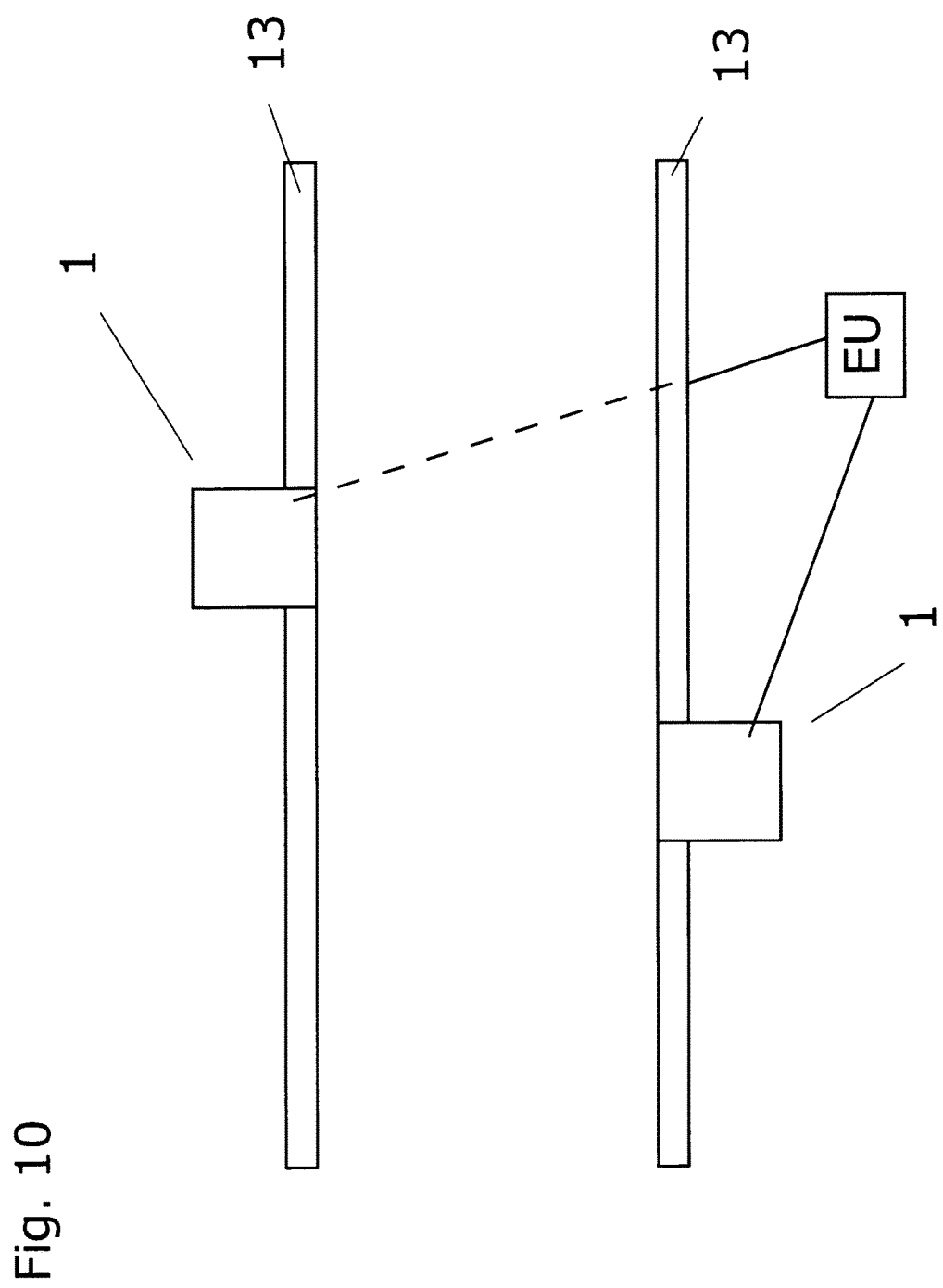
FIG. 10 shows the electronic units mounted on respective measuring tubes.

FIG. 10 shows the evaluation unit EU connected to ultrasonic measuring assemblies 1 located in measuring tubes 13.

The invention claimed is:

1. An ultrasonic transducer assembly, comprising:
at least a first and a second ultrasonic transducer mounting assembly, which are arranged on a measuring tube in such a way that ultrasonic signals can be transmitted from a first ultrasonic transducer of said first ultrasonic transducer mounting assembly to a second ultrasonic transducer of said second ultrasonic transducer mounting assembly, and vice versa, via the volume of said measuring tube, through which the medium flows, wherein said first and second ultrasonic transducer mounting assembly, each comprising:
an ultrasonic transducer element;
a transducer housing, in which said ultrasonic transducer element is arranged; and
an accommodation unit, wherein:
said transducer housing in said accommodating unit is clamped in a clamping path, said clamping path comprises two bearings with a plurality of rolling elements, for acoustically decoupling said transducer housing from said accommodating unit,
said transducer housing comprises a first and a second clamping surface and said accommodation unit comprises a first and a second clamping surface; and
a first of said two bearings is made of a plurality of rolling elements between said first clamping surface of said transducer housing and said first clamping surface of said accommodation unit, and a second of said two bearings is made of a plurality of rolling elements between said second clamping surface of said transducer housing and said second clamping surface of said accommodation unit,
wherein said rolling elements are held by one of: a bearing ring, and a cylindrical cover.

2. The ultrasonic transducer assembly according to claim 1, wherein:
said plurality of rolling elements of said bearings are barrel-shaped.

3. The ultrasonic transducer assembly according to claim 1, wherein:
said transducer housing in said accommodation unit is pre-tensioned in the clamping path by means of at least one spring.

4. The ultrasonic transducer assembly according to claim 3, wherein:
said least one spring is at least one disk spring.

5. The ultrasonic transducer assembly according to claim 3, wherein:
said least one spring is at least one helical spring.

6. The ultrasonic transducer assembly according to claim 1, wherein:
said plurality of rolling elements of said bearings are made of one of:
metal, ceramic, plastic, glass or a composite.

7. The ultrasonic transducer assembly according to claim 1, wherein:
said bearing ring or said cylindrical cover comprises a central axis; and said plurality of rolling elements are held such that a radial movement of said plurality of rolling elements is blocked or limited relative to said central axis.

8. The ultrasonic transducer assembly according to claim 7, wherein:
the blockage or limitation is either by the interaction of said rolling elements among themselves or by means of a central holder, which is arranged within said bearing ring or said cylindrical cover.

9. The ultrasonic transducer assembly according to claim 7, wherein:
the blockage or limitation is either by the interaction of said rolling elements among themselves or by means of a ring, which is arranged within said bearing ring or said cylindrical cover.

10. The ultrasonic transducer assembly according to claim 7, wherein:
the blockage or limitation is either by the interaction of said rolling elements among themselves or by means of an O-ring, which is arranged within said bearing ring or said cylindrical cover.

11. The ultrasonic transducer assembly according to claim 1, wherein said two bearings are ball bearings and said plurality of rolling elements are a plurality of balls.

* * * * *